United States Patent [19]

Sebag

[11] Patent Number: 5,614,181

[45] Date of Patent: Mar. 25, 1997

[54] NONIONIC SURFACTANTS DERIVED FROM 1,2-ISOPROPYLIDENE-3-EPOXYPROPYLGLYCEROL AND A CARBOXYLIC ACID AND THEIR USE

[75] Inventor: Henri Sebag, Paris, France

[73] Assignee: L'Oreal, Paris, France

[21] Appl. No.: 114,307

[22] Filed: Sep. 2, 1993

Related U.S. Application Data

[63] Continuation of Ser. No. 835,865, Feb. 18, 1992, abandoned, which is a continuation of Ser. No. 470,702, Jan. 26, 1990, abandoned.

[30] Foreign Application Priority Data

Jan. 26, 1989 [FR] France ..................... 89 00963

[51] Int. Cl.$^6$ .................................................. A61K 7/06
[52] U.S. Cl. .............. 424/70.31; 424/70.1; 424/70.11; 424/78.03; 514/937; 510/130; 510/119
[58] Field of Search ................ 424/450, 70.31, 424/70.1, 70.11, 78.03; 514/887, 937; 252/174.21

[56] References Cited

U.S. PATENT DOCUMENTS

| | | | |
|---|---|---|---|
| 3,674,902 | 7/1972 | Kalopissis et al. | 424/70.11 |
| 4,025,540 | 5/1977 | Kleeman et al. | 260/410.6 |
| 4,105,580 | 8/1978 | Sebag et al. | 252/351 |
| 4,126,702 | 11/1978 | Vanlerberghe et al. | 424/70.11 |
| 4,367,220 | 1/1983 | Boulogne et al. | 424/64 |
| 4,398,045 | 8/1983 | Sebag | 568/624 |
| 4,839,166 | 6/1989 | Grollir et al. | 424/70.11 |
| 4,897,308 | 1/1990 | Vanlerberghe et al. | 428/402.2 |
| 4,954,292 | 9/1990 | Hull et al. | 252/174.21 |

Primary Examiner—Raj Bawa
Attorney, Agent, or Firm—Cushman Darby & Cushman Intellectual Property Group of Pillsbury Madison & Sutro LLP

[57] ABSTRACT

A nonionic surfactant useful in a cosmetic composition has the formula

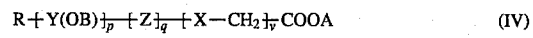

wherein R is an aliphatic, cycloaliphatic or alkylaryl radical containing 8–30 carbon atoms; Y is a trivalent radical selected

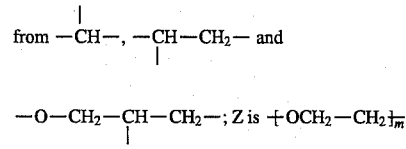

wherein m ranges from 1 to 20; X is —O—, —S— or —S=O; p, q and v represent 0 or 1 with the proviso that the sum p+q=0 or 1; and with the further provisos that when Y is

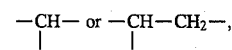

R is a saturated linear aliphatic radical and when Y is

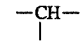

and p=1, v is 0; A represents $\{C_2H_3O(CH_2OCH_2-CHOH-CH_2OH)\}_aH$ and B represents $\{C_2H_3O(CH_2OCH_2CHOH-CH_2OH)\}_bH$ wherein a+b=n and n ranges from 1.5 to 8.

5 Claims, No Drawings

NONIONIC SURFACTANTS DERIVED FROM 1,2-ISOPROPYLIDENE-3-EPOXYPROPYLGLYCEROL AND A CARBOXYLIC ACID AND THEIR USE

This is a continuation of application Ser. No. 07/835,865, filed Feb. 18, 1992, now abandoned, which in turn is a continuation of application Ser. No. 07/470,702, filed Jan. 26, 1990, now abandoned.

BACKGROUND OF THE INVENTION

1. Field of the Invention

The invention relates to a new process for preparing nonionic surfactant compounds, to new nonionic surfactant compounds, to compositions containing them as well as to the use of these compositions in the cosmetics and pharmaceutical products industry.

The new process consists, in a first step, in condensing a compound containing a terminal carboxy-group with 1,2-isopropylidene-3-epoxypropylglycerol of formula (II):

$$CH_2\text{---}CH\text{---}CH_2\text{---}O\text{---}CH_2\text{---}CH\text{---}CH_2 \quad (II)$$
(with epoxide and isopropylidene-dioxy groups, CH₃, CH₃)

and then, in a second step, in hydrolyzing the products obtained, to prepare polyhydroxylated nonionic products.

2. Description of the Art

Polyhydroxylated nonionic surfactant compounds are known. In particular, French Patent No. 1,484,723 and U.S. Pat. No. 3,674,902 describe surfactant compounds of formula:

$$R\text{---}O\text{---}[C_2H_3O(CH_2OCH_2CHOH\text{---}CH_2OH)]_{\overline{n}}H \quad (F_1)$$

These products of formula ($F_1$) are obtained by the reaction of allyl glycidyl ether with a saturated or unsaturated fatty alcohol, followed by hydroxylation of the double bonds with "130 volumes" hydrogen peroxide in the presence of 98% strength formic acid for 24 to 48 hours at 40° C. The use of hydrogen peroxide and concentrated acid is always hazardous, both from the point of view of safety and from the point of view of the formation of the products, the hazards being due to peroxidation or derived from the epoxidation side reaction. Furthermore, during this 2nd step, in the case where unsaturated fatty alcohols such as oleyl alcohol, for example, are used, the double bond is hydroxylated, leading to the formation of two hydroxyl groups in the middle of the fatty chain; it is hence not possible to obtain compounds of formula ($F_1$) in which R denotes an unsaturated aliphatic radical.

The process of the present invention does not have these drawbacks.

SUMMARY OF THE INVENTION

The new process consists, in a first step, in condensing compounds of formula ($I_1$), in which the carboxy group is terminal, with 1,2-isopropylidene-3-epoxypropylglycerol of formula (II), and then, in a second step, in hydrolyzing the products obtained, of formula ($III_1$), according to the following general scheme, to polyhydroxylated nonionic products of formula ($IV_1$):

$$R_1COOH + {}_nCH_2\text{---}CH\text{---}CH_2\text{---}O\text{---}CH_2\text{---}CH\text{---}CH_2 \longrightarrow$$
($I_1$) \quad (II)

$$\longrightarrow R_1COO\text{---}[C_2H_3O(CH_2\text{---}O\text{---}CH_2\text{---}CH\text{---}CH_2)]_{\overline{n}}H$$
($III_1$)

$$\xrightarrow{H_2O, H^+} R_1COO\text{---}[C_2H_3O(CH_2\text{---}O\text{---}CH_2\text{---}CHOH\text{---}CH_2OH)]_{\overline{n}}H$$
($IV_1$)

The group $$C_2H_3O(CH_2\text{---}O\text{---}CH_2\text{---}CHOH\text{---}CH_2OH) \quad (V)$$

denotes one or another of the following groups $V_a$ and $V_b$, resulting from the two possible directions of opening of the epoxide group of (II):

$$\text{---}CH_2\text{---}CHO\text{---} \quad (V_a)$$
$$\quad\quad\quad |$$
$$\quad\quad CH_2$$
$$\quad\quad\quad |$$
$$\quad\quad O\text{---}CH_2CHOH\text{---}CH_2OH$$

et $$\text{---}CH\text{---}CH_2\text{---}O\text{---} \quad (V_b)$$
$$\quad |$$
$$\quad CH_2$$
$$\quad |$$
$$\quad O\text{---}CH_2\text{---}CHOH\text{---}CH_2OH$$

n denotes an integer or decimal number from 1 to 10, and preferably from 1.5 to 8, and represents the number of moles of epoxide of formula (II) employed per mole of carboxylic acid of formula ($I_1$). It represents, in the products of formula ($IV_1$), the average number of units (V) per fatty chain, it being possible for the actual number to be less than, equal to or more than the latter number.

$R_1$ is a radical derived from carboxylic acids of overall formula $R_1$—COOH ($I_1$), the general structural formula of which may be represented by the formula (I) below:

$$R\text{---}[Y(OH)]_{\overline{p}}\text{---}[Z]_{\overline{q}}\text{---}X\text{---}[CH_2]_{\overline{v}}COOH \quad (I)$$

in which:

R denotes an aliphatic radical or a cycloaliphatic or alkylaryl radical containing 8 to 30 carbon atoms;

Y denotes a trivalent radical such as $$\text{---}CH\text{---}, \text{---}CH\text{---}CH_2\text{---} \text{ or } \text{---}O\text{---}CH_2\text{---}CH\text{---}CH_2\text{---}.$$

In each case, the hydroxyl group is linked via a covalent bond to the tertiary carbon;

Z denotes —[OCH$_2$—CH$_2$]$_m$— where m denotes an integer or decimal number from 1 to 20;

X denotes —O—, —S— or S=O; and p, q and v denote 0 or 1, p+q=0 or 1.

When Y denotes $$\text{---}CH\text{---} \text{ or } \text{---}CH\text{---}CH_2\text{---},$$

then R denotes a saturated linear aliphatic radical.

When Y denotes

and p=1, then v=0.

The surfactant compounds of the invention may hence be represented by the following general formula (IV):

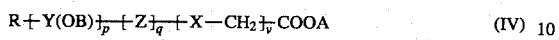     (IV)

in which R, X, Y, Z, p, q and v have the same meaning as above,

A denotes $-[C_2H_3O(CH_2OCH_2-CHOH-CH_2OH)]_a-H$ and

B denotes $-[C_2H_3O(CH_2OCH_2-CHOH-CH_2OH)]_b-H$   a+b=n.

In effect, when p=1, that is to say when the carboxylic acid contains a hydroxyl group, the latter is also capable of reacting with the epoxide of formula (II) and initiating another hydrophilic chain; in this case, the compounds of formula (IV) contain two hydrophilic moieties per hydrocarbon fatty chain.

Among acids of formula (I) which are usable according to the invention, there may be mentioned, by way of example:

alkanoic acids, alkenoic acids, alkylpolyenoic acids, α-hydroxyalkanoic acids, resin acids, lanolin acids;

(alkylpolyoxyethyloxy) methylenecarboxylic acids;

(alkylphenylpolyoxyethyloxy)methylenecarboxylic acids;

(3-alkyloxy-2-hydroxypropyloxy)methylenecarboxylic acids;

[3-(alkylphenyloxy)-2-hydroxypropyloxy]methylenecarboxylic acids;

(3-alkyloxy-2-hydroxypropylthio)methylenecarboxylic acids;

[3-(alkylphenyloxy)-2-hydroxypropylthio]methylenecarboxylic acids;

(2-hydroxyalkylthio)methylenecarboxylic acids.

DETAILED DESCRIPTION OF THE INVENTION

The process of the invention enables degradable polyhydroxylated nonionic surfactants, essentially containing one fatty chain per hydrophilic unit, to be obtained simply and directly from carboxylic acids, optionally of high molecular weight.

The products of the invention are surfactants which can be soluble or dispersible in water, depending on the nature of the hydrocarbon chain R and the number n of hydrophilic units.

For a given acid $R_1COOH$, the higher the value of n, the more hydrophilic the products and the lower their affinity for oils, and vice versa.

The process of the invention consists in reacting, by slow introduction, the epoxide of formula (II) with an acid of formula (I).

The reaction proceeds under a nitrogen atmosphere preferably in the presence of an alkaline catalyst such as sodium methylate, ethylate or t-butylate or potassium methylate, ethylate or t-butylate, at a temperature of between 80° and 155° C.

The reaction may be carried out without a solvent, or alternatively in an apolar solvent such as benzene, toluene or xylene.

Quantities from 3 to 10 mol % of catalyst relative to the acid of formula (I) are used.

The second step of the reaction consists in hydrolyzing the intermediate compounds of formula $(III_1)$. After any solvent has been removed, the reaction mixture is taken up in another solvent, in the presence of 2 to 50% of water and an inorganic or organic acid. A lower alcohol such as isopropanol is preferably used as a solvent for taking up the reaction mixture. An acid such as hydrochloric acid will be used as an inorganic acid, and an acid such as acetic acid, lactic acid or methanesulphonic acid as an organic acid.

The hydrolysis reaction is carried out at a temperature between 15° and 80° C., and preferably between 20° and 50° C., for 2 to 20 hours.

The production of products of formula (IV) in which X denotes S=O is carried out by oxidation of the products of formula (IV) in which X denotes a sulphur atom with 35% strength hydrogen peroxide and at a temperature of 20° to 50° C.

The surfactant products are then obtained by removal of the solvents and drying under reduced pressure after neutralization of the catalyst.

The subject of the invention is also the polyhydroxylated nonionic products of formula (IV).

They are soluble or dispersible in water. Depending on the case, the products possess foaming, emulsifying or dispersant properties. They can, moreover, be self-emulsifying, that is to say they can disperse readily in water giving stable milky dispersions which, where appropriate, take the form of vesicular microdispersions capable of transporting active substances.

The new nonionic products of the invention may be used as surfactants in cosmetic compositions for skin and hair care, for example foaming compositions such as shampoos, foam baths, cleansing compositions, face or body milks or creams, skin dyeing or coloring compositions, sun compositions and emollient or disentangling compositions.

These surfactant compounds can be readily combined with the various constituents generally present in cosmetic or pharmaceutical compositions.

They can be combined with other nonionic surfactants, with ionic surfactants, with natural or synthetic polymers, with mineral, animal or vegetable oils or waxes or with polysiloxane derivatives.

The subject of the invention is also compositions containing one or more compounds of formula (IV).

These compositions can contain, in addition, alcoholic solvents, propellants, thickeners, preservatives, sunscreens, coloring, fragrances, additives such as emulsifiers, sterols, moisturizing agents and active products for the treatment of skin or scalp conditions, for regrowth of the hair, and the like.

The compositions according to the invention can take various forms, in particular the form of a solution, aqueous-alcoholic lotion, oil-in-water or water-in-oil emulsion, microemulsion, microdispersion of lipid vesicles optionally containing active products optionally in the presence of oil, gel or bar, or of products for spraying.

The subject of the invention is also the use of the compositions containing a compound of formula (IV) or a product resulting from the preparation process described above, more especially in cosmetics or pharmaceutical fields.

The invention will be understood more fully by means of the non-limiting examples below.

PREPARATION EXAMPLES

EXAMPLE 1

Preparation of a mixture of compounds of formula (IV) in which:

R denotes a $C_{15}H_{31}$ radical, $p=q=v=0$, $a=n=3$.

1 g of sodium methylate in methanolic solution (5.6 meq.) is added to 17.5 g of palmitic acid (0.07 mole), followed by the addition of 13.16 g (0.07 mole) of epoxide of formula (II) in the course of 30 minutes at 80° C. The temperature is raised gradually to 145°–150° C., and a further 26.32 g (0.14 mole) of epoxide of formula (II) are then added in the space of one hour. The temperature and stirring are maintained for 2 hours.

The reaction mixture is taken up with 30 ml of isopropanol and 30 ml of normal hydrochloric acid, in three portions, at intervals of 1 hour, heating gently to 30°–35° C.

The acidity is neutralized with sodium hydroxide and the solvents are then evaporated off under reduced pressure.

A beige paste, soluble in water with very slight opalescence, is obtained.

EXAMPLE 2

Preparation of a mixture of compounds of formula (IV) in which:

R denotes the hydrocarbon radical derived from abietic acid, $p=q=v=0$, $a=n=4$.

0.71 g of methanolic sodium methylate solution containing 5.6 meq./g is added to 15.1 g of molten abietic acid (0.05 mole), followed by the addition of 9.4 g (0.05 mole) of epoxide of formula (II) in the course of 30 minutes at a temperature of 125°–130° C. The mixture is heated gradually to 150° C. during one hour, and 28.2 g (0.15 mole) of epoxide of formula (II) are then added.

After 8 hours' heating, the dark brown reaction mixture thereby obtained is washed with twice 100 ml of water at 30°–35° C. in the presence of 10 ml of dichloromethane.

The organic phase is taken up with 50 ml of isopropanol, 20 ml of water and 2 ml of concentrated hydrochloric acid, for 3 hours at 40° C.

The mixture is neutralized by adding concentrated sodium hydroxide and the solvents are then evaporated off under reduced pressure.

A highly colored, sticky and freely running water-soluble paste is obtained.

EXAMPLE 3

Preparation of a mixture of compounds of formula (IV) in which:

R denotes the hydrocarbon radical derived from oleic acid, $p=0$, $q=1$, $v=1$

Z denotes $-(OCH_2-CH_2)_m-$ where $m=5$ (average value)

$X=-O-$; $a=n=4$.

0.71 g of methanolic sodium methylate solution containing 5.6 meq./g is added to 30 g (0.05 mole) of (oleyloxypolyethoxy)methylenecarboxylic acid, sold by the company CHEMY under the name AKYPO RO 50, followed by the addition of 9.4 g (0.05 mole) of epoxide of formula (II) in the course of 30 minutes at 125° C. The mixture is then heated gradually to 150° C., and 28.2 g (0.15 mole) of epoxide of formula (II) are added thereafter.

The mixture is heated to 150° C. for 4 hours. 0.05 g of potassium t-butylate is also added and heating is continued for 2 hours.

The reaction mixture is taken up with 50 ml of isopropanol and 20 ml of normal hydrochloric acid, and the resulting mixture is heated with stirring for 8 hours at between 25° and 30° C.

After neutralization and evaporation of the solvent under reduced pressure, a dark-colored water-soluble product is obtained.

EXAMPLE 4

Preparation of a mixture of compounds of formula (IV) in which:

R denotes a $C_{15}H_{31}$ radical, $p=q=v=0$ and $a=n=1$.

4.3 g of methanolic sodium methylate solution containing 5.6 meq./g are added to 75 g of palmitic acid (0.3 mole), and the mixture is heated gradually to 120°–125° C. under a stream of nitrogen to remove the methanol. 56.4 g of epoxide of formula (II) are then added at this same temperature, in the course of 1 hour. Heating and stirring are maintained for 1 hour 30 minutes. The reaction mixture is cooled and taken up with 200 ml of isopropanol to which 30 ml of normal hydrochloric acid are added, and the mixture is stirred at 35° C. for 3 hours.

The excess acid is neutralized exactly with sodium hydroxide and the solvents are evaporated off under reduced pressure. A white water-dispersible wax is thereby obtained.

| APPLICATION EXAMPLES | |
|---|---|
| EXAMPLE A: shampoo | |
| Compounds of Example 2 | 3.0 g AS |
| Nonionic surfactant of formula: $R-CHOH-CH_2-O(CH_2-CHOH-CH_2O)_n-H$ | 10.0 g AS |
| where R is a $C_9-C_{12}$ alkyl n denotes an average statistical value of 3.5 | |
| Dimethyldistearylammonium chloride | 1.0 g AS |
| NaOH q.s. pH 7.0 | |
| Water | q.s. 100.0 g |
| EXAMPLE B: emollient milk for the body | |
| Compounds of Example 1 | 7.0 g AS |
| Compounds of Example 4 | 3.0 g AS |
| Liquid paraffin | 40.0 g |
| Water | q.s. 100.0 g |

The compounds of Examples 1 and 4 are solubilized in liquid paraffin by heating to 80°–90° C. The mixture is cooled to about 60° C. and the water, itself heated to 60° C., is added with vigorous stirring. A fine and stable emulsion is obtained.

AS=active substance.

I claim:

1. A nonionic surfactant having the formula

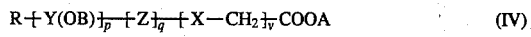  (IV)

wherein

R represents an aliphatic radical or a cycloaliphatic radical or an alkylaryl radical, containing 8 to 30 carbon atoms, Y represents a trivalent radical selected from the group consisting of

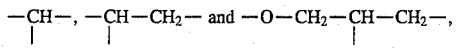

Z represents $-[OCH_2\text{-}CH_2]_m-$, wherein m represents an integer or decimal number ranging from 1 to 20, X represents a member selected from the group consisting of $-O-$, $-S-$ and $S=O$, p, q and v represent 0 or 1 with the proviso that the sum, p+q=0 or 1; and with the further proviso that (i) when Y represents

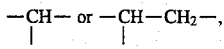

R represents a saturated linear aliphatic radical, and (ii) when Y represents

and p=1, v is equal to 0,

A represents $-[C_2H_3O(CH_2OCH_2-CHOH-CH_2OH)-]_aH$ and

B represents $-[C_2H_3O(CH_2-CHOH-CH_2OH)-]_bH$ wherein a+b=n and n represents an integer or decimal number ranging from 1.5 to 8.

2. The nonionic surfactant of claim 1 having the formula $C_{15}H_{31}-COO-[C_2H_3O(CH_2OCH_2-CHOH-CH_2OH)-]_nH$.

3. The nonionic surfactant of claim 1 having the formula $C_{15}H_{31}-COO-[C_2H_3O(CH_2OCH2-CHOH-CH_2OH)-]_3H$.

4. Cosmetic composition for application to the hair or skin consisting essentially of, in an aqueous vehicle suitable for application to said hair or skin, at least one nonionic surfactant having the formula

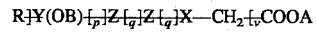 (IV)

wherein

R represents an aliphatic radical or a cycloaliphatic radical or an alkylaryl radical, containing 8 to 30 carbon atoms, Y represents a trivalent radical selected from the group consisting of

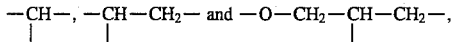

Z represents $-[OCH_2-CH_2]_m-$, wherein m represents an integer or decimal number ranging from 1 to 20, X represents a member selected from the group consisting of $-O-$, $-S-$ and $S=O$, p, q and v represent 0 or 1 with the proviso that the sum, p+q=0 or 1; and with the further proviso that (i) when Y represents

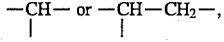

R represents a saturated linear aliphatic radical, and (ii) when Y represents

and p=1, v is equal to 0,

A represents $-[C_2H_3O(CH_2OCH_2-CHOH-CH_2OH)-]_aH$ and

B represents $-[C_2H_3O(CH_2OCH_2-CHOH-CH_2OH)-]_bH$ wherein a+b=n and n represents an integer or decimal number ranging from 1.5 to 8.

5. The cosmetic composition of claim 4 which further contains at least one component selected from the group consisting of a solvent; a propellant; a thickener; a preservative; a sunscreen agent; a coloring agent; a fragrance; an emulsifying agent; a sterol; and a moisturizing agent.

* * * * *